(12) United States Patent
Le Couedic et al.

(10) Patent No.: US 8,002,805 B2
(45) Date of Patent: Aug. 23, 2011

(54) INTERVERTEBRAL IMPLANT

(75) Inventors: Regis Le Couedic, Andresy (FR); Denis Pasquet, Quinsac (FR)

(73) Assignee: Zimmer Spine, Bordeaux (FR)

( * ) Notice: Subject to any disclaimer, the term of this patent is extended or adjusted under 35 U.S.C. 154(b) by 33 days.

(21) Appl. No.: 12/536,855

(22) Filed: Aug. 6, 2009

(65) Prior Publication Data
US 2010/0016897 A1 Jan. 21, 2010

Related U.S. Application Data

(63) Continuation of application No. 11/579,891, filed as application No. PCT/FR2005/001140 on May 9, 2005, now Pat. No. 7,588,601.

(30) Foreign Application Priority Data

May 11, 2004 (FR) ..................................... 04 05064

(51) Int. Cl.
*A61B 17/70* (2006.01)
(52) U.S. Cl. ...... 606/263; 606/246; 606/248; 623/17.16
(58) Field of Classification Search .... 623/17.11–17.16; 606/246–249, 279, 60, 61, 263
See application file for complete search history.

(56) References Cited

U.S. PATENT DOCUMENTS

| | | |
|---|---|---|
| D285,968 S | 9/1986 | Kinnett |
| 5,245,731 A | 9/1993 | Funathu |
| 5,496,318 A * | 3/1996 | Howland et al. .............. 606/249 |
| 5,645,599 A | 7/1997 | Samani |
| 5,836,948 A | 11/1998 | Zucherman et al. |
| 6,440,169 B1 | 8/2002 | Elberg et al. |
| 6,514,256 B2 | 2/2003 | Zucherman et al. |
| 6,761,720 B1 | 7/2004 | Senegas |
| 6,946,000 B2 | 9/2005 | Senegas et al. |
| 7,087,083 B2 | 8/2006 | Pasquet et al. |
| 7,163,558 B2 | 1/2007 | Senegas et al. |
| 7,238,204 B2 | 7/2007 | Le Couedic et al. |
| 7,588,601 B2 | 9/2009 | Le Couedic et al. |
| 7,635,377 B2 | 12/2009 | Zucherman et al. |
| 2006/0235532 A1 | 10/2006 | Meunier et al. |
| 2008/0033556 A1 | 2/2008 | Le Couedic et al. |

FOREIGN PATENT DOCUMENTS

WO 02071960 A1 9/2002

* cited by examiner

*Primary Examiner* — Todd E Manahan
*Assistant Examiner* — Christina Negrelli
(74) *Attorney, Agent, or Firm* — Seager, Tufte & Wickhem LLC

(57) ABSTRACT

The invention relates to an intervertebral implant comprising a spacer constituted by first and second parts (12, 14), said parts being provided with mutual assembly means comprising first clip-fastener means (54, 56) secured to one of said parts, second clip-fastener means (49, 50) secured to the other part and suitable for cooperating with the first clip-fastener means to achieve releasable clip-fastening between the two parts, and guide means for guiding the two parts (12, 14) during clip-fastening, said guide means being distinct from the clip-fastening means and comprising:
   a substantially non-deformable first guide assembly (42, 44) secured to one of said parts; and
   a substantially non-deformable second guide assembly (46, 48) secured to the other part to co-operate with the first guide assembly.

20 Claims, 2 Drawing Sheets

INTERVERTEBRAL IMPLANT

CROSS REFERENCE TO RELATED APPLICATIONS

This application is a continuation of U.S. patent application Ser. No. 11/579,891, filed Nov. 9, 2006, and entitled "INTERVERTEBRAL IMPLANT," now pending, which is a 371 application of PCT/FR05/01140, filed on May 9, 2005, which claims priority to FR 0405064, filed May 11, 2004, which are all herein incorporated by reference.

TECHNICAL FIELD

The present invention relates to an intervertebral implant for an ordinary portion of the spinal column, and more particularly the invention relates to the spacer of the implant.

BACKGROUND

Intervertebral spacers are devices that are well known for placing between two adjacent vertebrae in order to secure the two vertebrae to each other so as to maintain a fixed gap between them. French patent application FR 01/03362 in the name of the Applicant describes such spacers. It suffices to recall that the spacer is provided at each of its ends with a notch in which the spinous process of a vertebra is engaged. A system of ties or braids serves to secure each end of the spacer with the spinous process.

Nevertheless, putting such a spacer into place raises certain problems associated with the practice of surgery. There is a ligament known as the supraspinous ligament that interconnects the tips of all the spinous processes. In order to put the spacer into place, it is necessary to move that ligament. In practice, it is detached from the two spinous processes concerned, and it is moved away by means of a suitable surgical instrument. To detach the ligament from the spinous processes, a scalpel is used. Once the spacer has been put into place, the ligament is sewn back onto the spinous processes after making a small opening therein to receive the suture.

The major drawback of that surgical technique is that by acting on the ligament in order to detach it and then move it out of the way, it is weakened mechanically. In addition, all of those actions take time, which lengthens the duration of the surgery.

To remedy that drawback, proposals have already been made for intervertebral spacers that are made up of from two distinct portions. Each portion of the spacer is put into place on either side of the supraspinous ligament, and then by using appropriate surgical instruments, the two portions of the spacer are joined together. Such two-portion spacers are described in particular in U.S. Pat. No. 6,156,038. Nevertheless, the two-portion spacers described in that document are relatively difficult to use. In particular, assembling the two portions of the spacer together in situ is relatively difficult and it is not certain that the two parts will together form the spacer in suitable manner.

SUMMARY

An object of the present invention is to provide an intervertebral spacer constituted by two distinct parts that are easier for the surgeon to assemble during surgery.

To achieve this object, according to the invention, in an intervertebral implant comprising a spacer constituted by first and second parts provided with mutual assembly means, the implant is characterized in that said mutual assembly means comprise:

first clip-fastener means secured to one of said parts;
second clip-fastener means secured to the other part, suitable for co-operating with the first clip-fastener means to achieve releasable clip-fastening between the two parts in a clip-fastening direction, said first and second clip-fastening means forming integral portions of the two parts; and
guide means for guiding the two parts during clip-fastening, said guide means being distinct from the clip fastener means and comprising:
a substantially non-deformable first guide assembly secured to one of said parts; and
a substantially non-deformable second guide assembly secured to the other part to co-operate with the first guide assembly so as to provide mutual guidance of the two parts along said clip-fastening direction and provide relative positioning of the two parts in a plane orthogonal to the clip-fastening direction.

It will be understood that because each part constituting the intervertebral spacer includes firstly guide means and secondly clip-fastener means, the guide means guarantee accurate relative positioning of the clip-fastener means in a manner that is easy for the surgeon. This ensures that the two parts constituting the spacer are properly assembled together, and furthermore, that this operation can be implemented more quickly than with the spacers of the prior art.

In addition, since the clip-fastener means form integral portions of the two parts, the implant is made easier for the surgeon to put into place.

In a preferred embodiment of the invention, each part of the spacer has an assembly face that is to be pressed against the assembly face of the other part when the two parts are assembled together.

Also preferably, the guide means are constituted respectively by two guide studs projecting from one of the assembly faces and by two recesses opening out into the assembly face of the other part. It is thus possible to obtain effective guidance of one of the parts relative to the other by giving the guide studs an appropriate shape.

BRIEF DESCRIPTION OF THE DRAWINGS

Other characteristics and advantages of the invention appear better on reading the following description of an embodiment of the invention given by way of non-limiting example. The description refers to the accompanying figures, in which.

DETAILED DESCRIPTION

Figure 1:
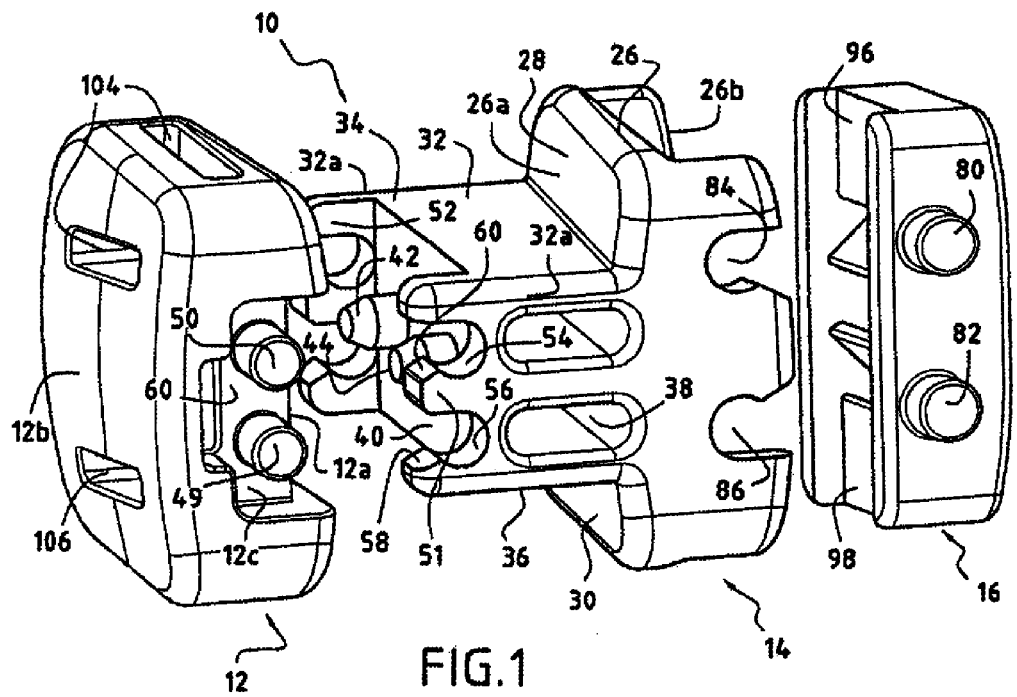
FIG. 1 is an exploded view of the various elements constituting the intervertebral implant.
Figure 2:
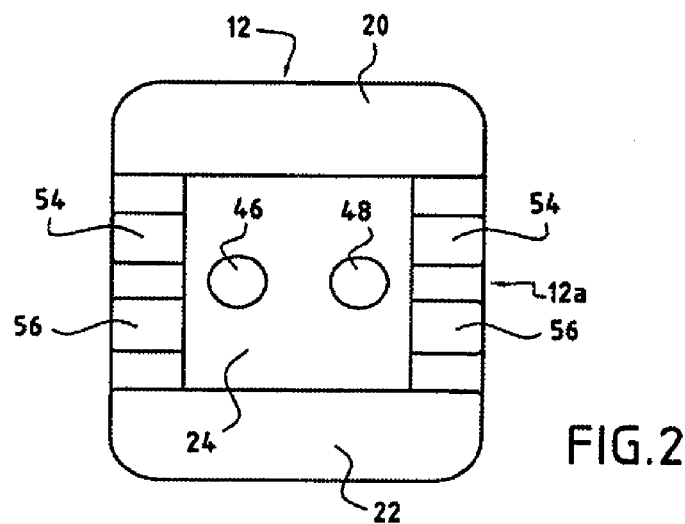
FIG. 2 is an assembly face view showing one of the two parts constituting the intervertebral spacer.

FIG. 1 shows the two parts 12 and 14 which are being assembled together serve to produce the intervertebral spacer 10. In the figure, there can also be seen a removable element 16 used for fastening purposes and for clamping braids that serve to secure two spinous processes to the spacer. The fastener element 16 is described below. The part 12 constitutes a first side piece of the intervertebral spacer. This part 12 has an inside face 12a and an outside face 12b. The inside face 12a defines a top bearing surface 20, a bottom bearing surface 22, and a middle assembly face 24.

The second part 14 also constitutes a side piece presenting an inside face 26a facing towards the inside face 12a of the part 12, and an outside face 26b. The inside face 26a of the side piece 26 defines a top bearing surface 28 and a bottom bearing surface 30. In the middle region of the inside face of the side piece 26, the part 14 has a projection 32 that projects from the central portion of the face 26a. This projection 32 or space-defining part defines two bearing surfaces, a top surface 34 and a bottom surface 36, these two faces being substantially parallel. The space-defining part 32 may include transverse recesses such as 38 for imparting a degree of resilience to this portion of the spacer. The free end of the space-defining part 32 defines an assembly face 40 for bearing against the assembly face 24 of the part 12 when the two parts constituting the spacer are assembled together.

In the assembly faces 40 and 24 of the two parts, there are provided mutual guidance means that act as these two parts move towards each other in order to 35 secure them one to the other. Preferably, the guidance means are constituted by two guide studs 42 and 44 projecting from the assembly face 40 of the part 14 and by two blind recesses 46 and 48 formed in the assembly face 24 of the part 12. It would not go beyond the invention if only one stud were to be provided together with only one recess. Preferably, and in conventional manner, the ends of the assembly studs 42 and 44 are conical in order to provide initial positioning of the two parts. The parts 12 and 14 are secured to each other by clip-fastener means formed respectively in the side faces 12c and 12d of the part 12 and in the side faces 32a and 32b of the projection 32 of the part 14. By way of example, for the part 12 these clip-fastener means consist of two pairs of cylindrical pegs 49 and 50 and of two side walls projecting beyond the assembly face 44 of the part 14, given respective references 51 and 52. Each side wall is provided with two openings 54 and 56 suitable for receiving the pegs 49 and 50 during clip-fastening. Each opening 54, 56 includes a deformable nib 58 or 60. As also shown in FIG. 1, the pegs 49 and 50 project into a recess 60 formed in the side faces 12c, 12d of the part 12. It should naturally be added that the guide studs 42 and 44 are of a length that is longer than that of the side walls 51 and 52 defining the female clip-fastener elements. Whatever the particular implementation of the clip-fastener means, they should form integral portions respectively of the two parts 12 and 14.

Figure 3:
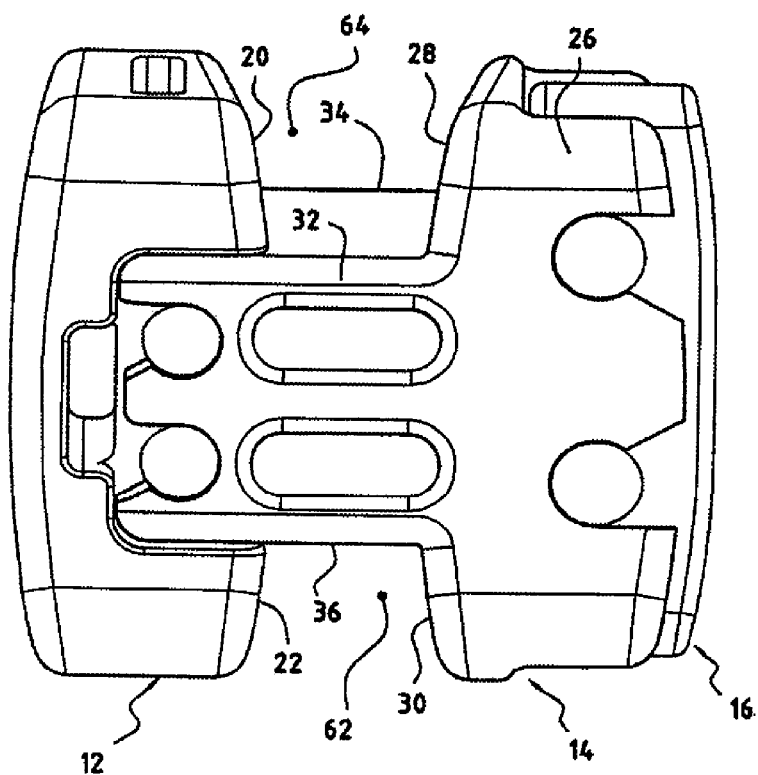
FIG. 3 is a side view of the spacer after the two parts constituting it have been assembled together.

As shown more clearly in FIG. 3, when the parts 12 and 14 are assembled together, in the manner explained below, an intervertebral spacer is obtained having the usual structure. In particular, the bearing faces 20, 22 of the part 12 and the bearing faces 28, 30 of the side piece 26 of the part 14, and finally the top and bottom faces 34 and 36 of the extension 32 define two recesses 62 and 64 for receiving the spinous processes of the two vertebrae between which the spacer is placed.

Naturally, it should be added that the guide studs 42 and 44 are of a length that is greater than that of the side walls 51 and 52 defining the female clip-fastener elements.

The above-described spacer is used as follows. The surgeon puts the spacer-constituting parts 12 and 14 into place, going round the supraspinal ligament. Using appropriate surgical instruments, the two parts are moved towards each other so as to cause the guide studs 42 and 44 to co-operate with the guide recesses 46 and 48. When the resulting relative positioning is achieved, the clip-fastener members 48, 50 and 54, 56 face one another in pairs. It then suffices for the surgeon to exert pressure on the outside faces of the two parts in order to cause the parts 12 and 14 to clip together, thus obtaining the complete spacer 10. It should be added that the clip-fastener elements 48, 50 and 54, 56 are made in such a manner as to ensure effective fastening, while still making it possible for them to be separated in the event of it being necessary to change the spacer. As explained above, it is easy to put the spacer into place since it comprises only two parts.

Figure 4:
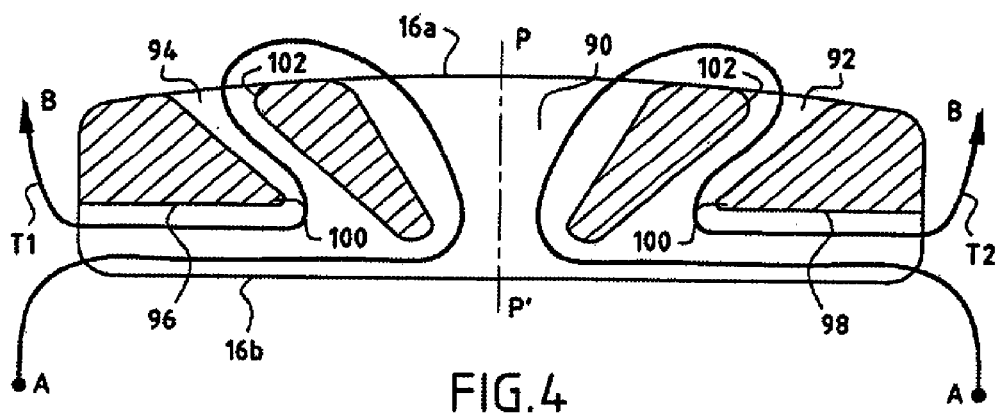
FIG. 4 is a longitudinal section of the self-locking element used for securing the braids of the implant.

With reference now to FIGS. 1 and 4, there follows a description of a preferred embodiment of the means for securing the spacer 10 to the spinous processes of the vertebrae. This system is constituted by the locking or fastener part 16 and by two braids T1 and T2. The fastener part 16 can be secured to the outside face 26b of the part 14 by clip-fastener means 80, 82, 84, and 86 that are identical to the clip-fastener means of the parts 12 and 14.

The fastener part 16 presents a clip-fastener face 16b on the part 14 and an outside face 16a. The fastener part 16 presents a plane of symmetry P, P' orthogonal to the faces 16a and 16b and parallel to the faces 32 and 34 of the extension 30 of the part 14. The locking part 16 has a central slot 90 that opens out into both faces of the part 16, and two symmetrical inclined side slots 92 and 94 that also open out into both faces of the part 16.

The clip-fastener face 16b of the part 16 presents two setback surfaces 96 and 98 that extend respectively between the side slots 92 and 94 and the top and bottom ends of the part 16 which constitutes braid clamping surfaces. The slot 92 and the setback surface 98 define a first sharp edge 100. Similarly, the slot 92 and the outside face 16a of the part 16 define a second sharp edge 102 that is parallel to the edge 100. As shown in the figure, the edge 102 is further away from the midplane P, P' than is the edge 100. In addition, it should be specified that the clamping surfaces 96 and 98 are disposed in such a manner that when the part 16 is clipped onto the spacer, the distance between the face 26b of the spacer and the surface 96 or 98 is slightly less than twice the thickness of the braids T1 and T2.

Each braid T1 and T2 has a first end A that is secured to the part 12. To do this, in the example described, the part 12 is provided with a top slot 104 and a bottom slot 106 in which the ends A of the braid can form a loop. After this loop has been stitched together, the braids T1 and T2 are effectively secured to each end of the part 12. The braid T2 is engaged between the surface 98 and the face 26b of the spacer and then in the central slot 90. Thereafter, it passes over a portion of the outside face 16a of the part 16 and penetrates into the slot 62, passing over the edge 102. Thereafter, the braid T2 is engaged under the presser surface 98, between the first strand of the same braid and said surface. When the surgeon exerts traction on the end B of the braid T2, that serves to clamp the braid T2 against the spinous process of the upper or lower vertebra. The braid T1 is naturally engaged in the part 16 in the same manner in order to provide a connection with the spinous process of the other vertebra.

It will be understood that the fastener part 16 act for each of the braids as a self-locking system. When the surgeon exerts traction on the free end B of the braid, it can move without excessive friction in the slots 90 and 92 until the desired clamping effect is obtained. In contrast, when no traction is exerted on the end B of the braid, i.e. when the intervertebral implant is in normal use, a self-locking effect is obtained by the presence of the sharp edges 100 and 102 and the clamping effect of the presser surface 98 on the two strands of the braid.

In a preferred embodiment, the first clip-fastener means comprise at least two male clip-fastener members 54 and 56 that are substantially undeformable, being disposed on either side of the assembly surface 24, and second clip-fastener means comprising at least two clip-fastener female members 49 and 50 that are elastically deformable and disposed on either side of the assembly surface 40.

Also preferably, said first guide assembly comprises at least one guide stud 42 and 44 projecting from an assembly face 40 of one of the parts and at least one recess 46 and 48 opening out into the assembly face 24 of the other part.

We claim:

1. An intervertebral implant for placement between the spinous processes of adjacent vertebrae, the intervertebral implant comprising:
   a first part;
   a second part having a first side and an opposite second side, the first part configured to be coupled to the first side of the second part;
   a fastening part having a first side and an opposite second side, the fastening part configured to be coupled to the second side of the second part with the first side of the fastening part facing the second side of the second part, the fastening part including a slot extending through the fastening part from the first side of the fastening part to the second side of the fastening part;
   a first band having a first end secured to the first part and a second free end configured to extend through the slot of the fastening part; and
   a second band having a first end secured to the first part and a second free end configured to extend through the slot of the fastening part.

2. The intervertebral implant of claim 1, wherein the fastening part includes a first inclined slot extending through the fastening part from the first side of the fastening part to the second side of the fastening part, and the fastening part includes a second inclined slot extending through the fastening part from the first side of the fastening part to the second side of the fastening part.

3. The intervertebral implant of claim 2, wherein the first band is configured to extend through the first inclined slot and the second band is configured to extend through the second inclined slot.

4. The intervertebral implant of claim 3, wherein the fastening part includes first and second presser surfaces each facing the second side of the second part, wherein a first side wall of the first inclined slot converges with the first presser surface at a first edge and a first side wall of the second inclined slot converges with the second presser surface at a second edge.

5. The intervertebral implant of claim 4, wherein a second side wall of the first inclined slot converges with the second side of the fastening part to define a third edge and a second side wall of the second inclined slot converges with the second side of the fastening part to define a fourth edge.

6. The intervertebral implant of claim 5, wherein the fastening part is symmetrical about a plane of symmetry.

7. The intervertebral implant of claim 6, wherein the first edge is closer to the plane of symmetry than the third edge and the second edge is closer to the plane of symmetry than the fourth edge.

8. The intervertebral implant of claim 7, wherein when the fastening part is coupled to the second part, the first and second presser surfaces are positioned a distance away from the second side of the second part no greater than twice the thickness of either band.

9. The intervertebral implant of claim 1, wherein the fastening part is symmetrical about a plane of symmetry.

10. The intervertebral implant of claim 9, wherein the slot of the fastening part is centered on the plane of symmetry of the fastening part.

11. The intervertebral implant of claim 10, wherein the fastening part includes a first inclined slot extending through the fastening part from the first side of the fastening part to the second side of the fastening part, and the fastening part includes a second inclined slot extending through the fastening part from the first side of the fastening part to the second side of the fastening part.

12. The intervertebral implant of claim 11, wherein the first and second inclined slots are symmetrically positioned on either side of the plane of symmetry.

13. An intervertebral implant for placement between the spinous processes of adjacent vertebrae, the intervertebral implant comprising:
   a first part having a first side and an opposite second side;
   a second part having a first side and an opposite second side, the first part configured to be coupled to the first side of the second part with the second side of the first part facing the first side of the second part;
   a fastening part having a first side and an opposite second side, the fastening part configured to be coupled to the second side of the second part with the first side of the fastening part facing the second side of the second part;
   a first band having a first end secured to the first part and a second free end configured to pass between the second side of the second part and the first side of the fastening part when the fastening part is coupled to the second part; and
   a second band having a first end secured to the first part and a second free end configured to pass between the second side of the second part and the first side of the fastening part when the fastening part is coupled to the second part.

14. The intervertebral implant of claim 13, wherein the second side of the first part includes one or more recesses extending into the first part, and the first side of the second part includes one or more projections for mating with the one or more recesses to align the first part with the second part when coupling the first part to the second part.

15. The intervertebral implant of claim 14, wherein the first part includes one or more first clip-fastening elements and the second part includes one or more second clip-fastening elements configured to mate with the one or more first clip-fastening elements when the first part is coupled to the second part.

16. The intervertebral implant of claim 15, wherein during coupling the first part to the second part, the one or more projections mates with the one or more recesses before the one or more first clip-fastening elements mates with the one or more second clip-fastening elements.

17. The intervertebral implant of claim 13, wherein the fastening part includes a slot extending through the fastening part between the first side of the fastening part and the second side of the fastening part, the slot having a width suitable for receiving both the first band and the second band.

18. The intervertebral implant of claim 17, wherein the fastening part includes first and second inclined slots extending through the fastening part, the first inclined slot having a width suitable for receiving the first band and the second inclined slot having a width suitable for receiving the second band.

19. The intervertebral implant of claim 18, wherein the fastening part includes first and second presser surfaces facing the second side of the second part, wherein a distance between each of the first and second presser surfaces and the second side of the second part is no greater than twice the thickness of either band.

20. The intervertebral implant of claim 19, wherein when the fastening part is coupled to the second part, the first band is pressed between the first presser surface and the second side of the second part and the second band is pressed between the second presser surface and the second side of the second part.

* * * * *